US008007433B2

(12) United States Patent
Iketani

(10) Patent No.: US 8,007,433 B2
(45) Date of Patent: Aug. 30, 2011

(54) ELECTRONIC ENDOSCOPE

(75) Inventor: Kohei Iketani, Saitama (JP)

(73) Assignee: Hoya Corporation, Tokyo (JP)

(*) Notice: Subject to any disclaimer, the term of this patent is extended or adjusted under 35 U.S.C. 154(b) by 1415 days.

(21) Appl. No.: 11/464,531

(22) Filed: Aug. 15, 2006

(65) Prior Publication Data

US 2007/0041720 A1 Feb. 22, 2007

(30) Foreign Application Priority Data

Aug. 18, 2005 (JP) ................................. 2005-237392

(51) Int. Cl.
*A61B 1/05* (2006.01)

(52) U.S. Cl. ......................... 600/110; 600/101; 600/112

(58) Field of Classification Search ........... 600/101–112
See application file for complete search history.

(56) References Cited

U.S. PATENT DOCUMENTS

| | | | | |
|---|---|---|---|---|
| 5,590,660 | A | 1/1997 | MacAulay et al. | |
| 5,827,190 | A | 10/1998 | Palcic et al. | |
| 6,088,606 | A * | 7/2000 | Ignotz et al. | 600/316 |
| 6,099,466 | A * | 8/2000 | Sano et al. | 600/160 |
| 6,686,949 | B2 | 2/2004 | Kobayashi et al. | |
| 6,697,101 | B1 | 2/2004 | Takahashi et al. | |
| 6,858,004 | B1 | 2/2005 | Ozawa et al. | |
| 6,945,928 | B2 | 9/2005 | Kobayashi et al. | |
| 2002/0014595 | A1 | 2/2002 | Sendai et al. | |
| 2003/0176768 | A1 | 9/2003 | Gono et al. | |
| 2003/0216626 | A1* | 11/2003 | Tsujita et al. | 600/321 |
| 2005/0104989 | A1 | 5/2005 | Shizukuishi | |

FOREIGN PATENT DOCUMENTS

| | | |
|---|---|---|
| JP | 5-228109 | 9/1993 |
| JP | 6-054792 | 3/1994 |
| JP | 10-500588 | 1/1998 |
| JP | 10-309282 | 11/1998 |
| JP | 11-104061 | 4/1999 |
| JP | 2002-045330 | 2/2002 |
| JP | 2002-330919 | 11/2002 |
| JP | 2003-018467 | 1/2003 |
| JP | 2003-153850 | 5/2003 |
| JP | 2004-258497 | 9/2004 |
| JP | 2005-151077 | 6/2005 |
| JP | 2005-198794 | 7/2005 |

OTHER PUBLICATIONS

U.S. Appl. No. 11/464,505 to Iketani, which was filed on Aug. 15, 2006.

English language Abstract of JP 2005-198794.

Japan Office action, dated Nov. 16, 2010 along with an english translation thereof.

* cited by examiner

*Primary Examiner* — Henry M Johnson, III
*Assistant Examiner* — Aaron Roane
(74) *Attorney, Agent, or Firm* — Greenblum & Bernstein, P.L.C.

(57) ABSTRACT

An electronic endoscope according to the present invention has a video-scope that has a first image sensor and a second image sensor, and a light supplier that selectively irradiates white light and excitation-light on an observed portion. The electronic endoscope further has a first color filter that has spectral transmitting characteristics, such that light having a first wavelength range corresponding to blue color is transmitted, and a second color filter that has spectral transmitting characteristics, such that light having a second wavelength range corresponding to green and red colors is transmitted. The electronic endoscope has a first signal processor, a second signal processor, and a third signal processor. The first signal processor generates normal image video signals. The second signal processor generates narrow-band video signals. The third signal processor generates auto-fluorescent video signals.

17 Claims, 11 Drawing Sheets

<NORMAL OBSERVATION IMAGE>

<NARROW-BAND IMAGE AND AUTO-FLUORESCENT IMAGE>

30'
AUTO-FLUORESCENT SIGNAL PROCESSOR
38
NORMAL IMAGE SIGNAL PROCESSOR
40
NARROW-BAND SIGNAL PROCESSOR
36
VIDEO SIGNAL CIRCUIT
42
RGB
Y/C
Video
70
SYSTEM COTROL CIRCUIT
44
LAMP
32
35
34
14A
14
LASER
47
LASER DRIVER
49
10'
10B
CCD DRIVER
17
ROM
15
19
14
12'B
12'A
13'B
13'A
14B
CF
18'B
18'A
10A
16

| | | | |
|---|---|---|---|
| G | R | G | R |
| R | G | R | G |
| G | R | G | R |
| R | G | R | G |

ELECTRONIC ENDOSCOPE

BACKGROUND OF THE INVENTION

1. Field of the Invention

The present invention relates to an electronic endoscope that is capable of displaying an auto-fluorescent image for diagnosing a lesion, such as a cancer, and an observed image generated by light having wavelengths of narrow-band in visible light, in addition to a normal full-color image.

2. Description of the Related Art

In an electronic endoscope, a so called "narrow-band image", which is generated by light having a narrow wavelength range, can be displayed in addition to a normal full-color image. Capillaries close to the surface of the epithelial layer reflect light having short wavelengths; on the other hand, organs in a deep portion in the epithelial layer reflect light having long wavelengths. Therefore, by arranging a color filter that transmits light having short wavelengths or long wavelengths, the capillaries or the organs in the epithelial layer are clearly displayed as a narrow-band image.

Further, by irradiating light, which has wavelengths in the ultraviolet range or in that vicinity (hereinafter, called "excitation-light"), an image based on fluorescent light (hereinafter, called an "auto-fluorescent image") can be displayed on a monitor. Tissue in the epithelial layer has a fluorescent substance, which emits fluorescent light (hereinafter, called "auto-fluorescent light") when the excitation-light is illuminated thereon. An object image is formed on an image sensor by the fluorescent light passing through an objective lens. Since the amount of auto-fluorescent light, which is emitted from a lesion or a piece of abnormal tissue, is weak compared to that emitted from the normal tissue, luminance of the lesion or the area adjacent to the lesion in an auto-fluorescent image is relatively small; thus, the lesion can be easily detected compared with the normal full-color image obtained by white light.

To display the normal image and the narrow-band image, for example, two rotating color filters, each of which has different color elements, are coaxially arranged along a light-path, and the imaging process is performed in accordance with the color sequential method. One color filter has spectral transmitting characteristics corresponding to human vision, and the other color filter has spectral transmitting characteristics such that some discrete narrow-band wavelengths are distributed. When displaying the normal image, the color filters are moved along a direction perpendicular to the light-path such that the one color filter corresponding to the perception is disposed on the light-path, and when displaying the narrow band image, the other color filter is arranged on the light-path. Further, to display the auto-fluorescent image, the other color filter is replaced with a filter for the auto-fluorescent image.

SUMMARY OF THE INVENTION

An object of the present invention is to provide an electronic endoscope system that is capable of displaying a normal full-color image, a narrow-band image, and an auto-fluorescent image without a blur.

An electronic endoscope according to the present invention has a video-scope that has a first image sensor and a second image sensor, and a light supplier that selectively irradiates white light and excitation-light on an observed portion. The electronic endoscope further has a first color filter and a second color filter. The first color filter is disposed on a light-path oriented toward the first image sensor, and has spectral transmitting characteristics, such that light having a first wavelength range corresponding to blue color is transmitted. The second color filter that is disposed on a light-path oriented toward the second image sensor, and has spectral transmitting characteristics, such that light having a second wavelength range corresponding to green and red colors is transmitted. The electronic endoscope has a first signal processor, a second signal processor, and a third signal processor. The first signal processor generates normal image video signals corresponding to a normal observation image on the basis of image-pixel signals that are read from the first and second image sensors by the white light. The second signal processor generates narrow-band video signals corresponding to a narrow-band image on the basis of image-pixel signals that are read from the first image sensor by reflected light of the excitation-light. The third signal processor generates auto-fluorescent video signals corresponding to an auto-fluorescent image on the basis of image-pixel signals that are read from the second image sensor by auto-fluorescent light emitted from the observed portion.

For example, the first wavelength range is set to a range that does not exceed a boundary wavelength in a range between 450 nm and 550 nm. The second wavelength range may be set to a range that exceeds the boundary wavelength.

For example, a change member for changing the mode is provided. The change member is operated to set a normal observation mode for displaying the normal observation image or the set a special observation mode for displaying the auto-fluorescent image and the narrow-band image.

To express a change of color clearly, the first color filter may a first plurality of color elements that have different spectral peak levels in a plurality of distributed curved lines, which are defined by the plurality of color elements. Also, the second color filter comprises a second plurality of color elements that have different spectral peak levels in a plurality of distributed curved lines, which are defined by the plurality of color elements. For example, the first color filter comprises three color elements that have spectral peak levels distributed at even intervals, and the second color filter comprises two or three color elements that have spectral peak levels distributed at even intervals.

To obtain the normal observation image, the narrow-band image, and the auto-fluorescent image by using only one optical system, for example, one objective optical system that forms an object image, and a beam splitter are provided. The beam splitter divides light passing through the objective optical system into light having the first wavelength range and light having the second wavelength range. An object image is formed on the first image sensor by the light having the first wavelength range, and an object image is formed on the second image sensor by the light having the second wavelength range.

On the other hand, when using two optical systems, for example, a first objective optical system that forms an object image on the first image sensor, and a second objective optical system that forms an object image on the second image sensor, are provided. A cut-off filter may be disposed at the front of the second objective optical system. The cut-off filter blocks the light having the first wavelength range.

When using one light source, for example, a light source that emits white light having spectral transmitting characteristics in which spectrum is distributed over wavelengths of visible light, an excitation-color filter, and a color filter driver may be provided. The excitation-light color filter transmits light having a wavelength range corresponding to the excitation-light. The color filter driver that selectively positions the excitation-light color filter on a light-path and off the light-path. For example, the color filter driver positions the excitation-light color filter on a light-path when a normal observation mode for displaying the normal observation image is set, and positions the excitation-light color filter off the light-path when a special observation mode for displaying the auto-fluorescent image and the narrow-band image is set.

On the other hand, when using a laser, a white light source that emits white light having spectral transmitting characteristics in which spectrum is distributed over wavelengths of visible light, a laser that emits the excitation-light, an optical system that directs the excitation-light to a light-path of the white light, and a laser driver that turns the laser ON/OFF, are provided.

Preferably, a fourth signal processor that processes the auto-fluorescent video signals and the NBI video signals so as to display the auto-fluorescent image and the narrow-band image on a monitor separately and simultaneously, is provided. When using one monitor, for example, a fifth signal processor that selectively outputs one of the normal image video signals and a set of the NBI video signals and auto-fluorescent video signals, may be provided.

BRIEF DESCRIPTION OF THE DRAWINGS

The present invention will be better understood from the description of the preferred embodiments of the invention set forth below together with the accompanying drawings, in which.

DESCRIPTION OF THE PREFERRED EMBODIMENTS

Hereinafter, the preferred embodiments of the present invention are described with reference to the attached drawings.

Figure 1:
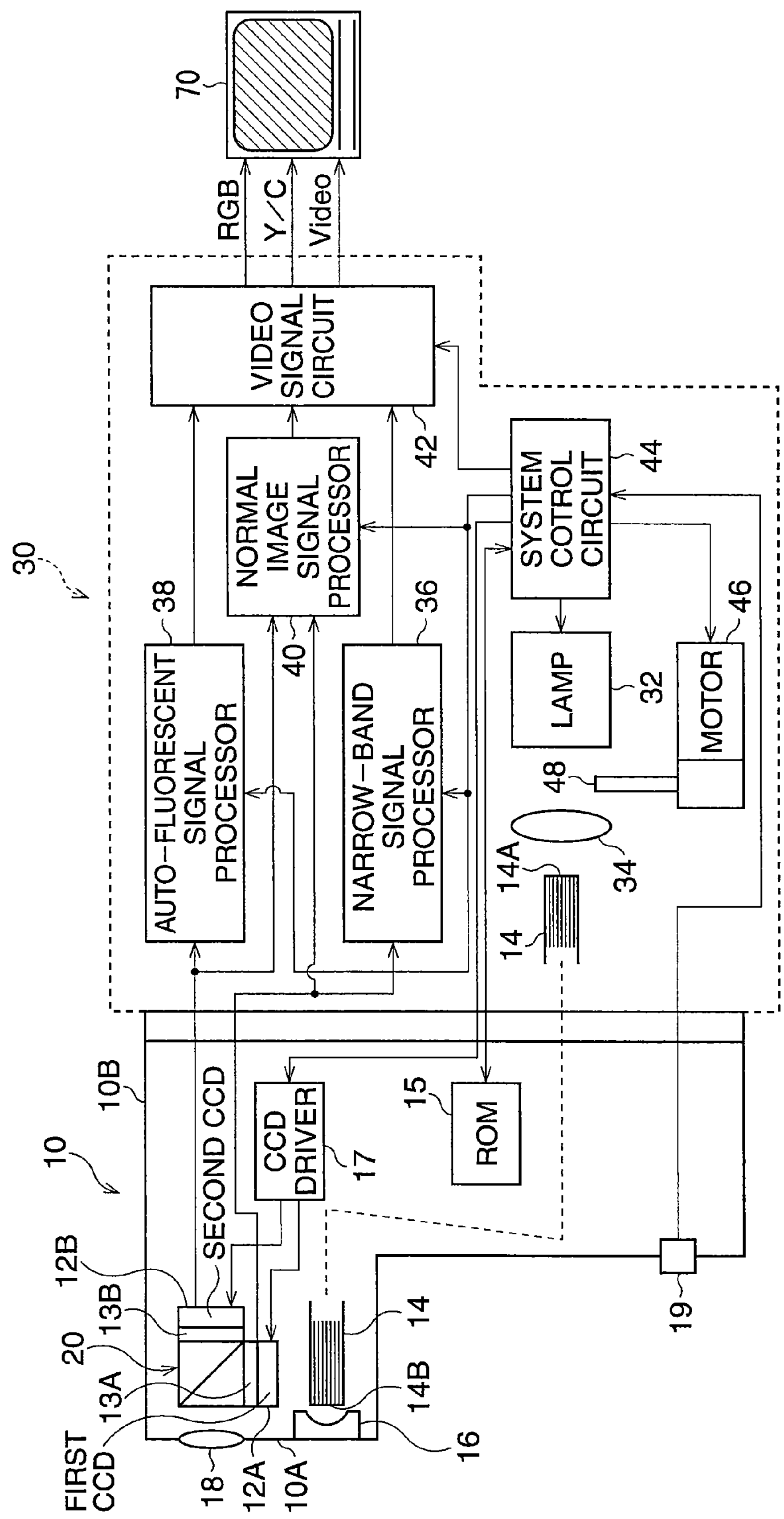
FIG. 1 is a block diagram of an electronic endoscope according to a first embodiment.

FIG. 1 is a block diagram of an electronic endoscope according to a first embodiment. An electronic endoscope has a video-scope 10 and a video-processor 30, and a monitor 70 is connected to the video-processor 30. The video-scope 10 is removably attached to the video-processor 20.

In the video-processor 30, a lamp 32, such as a xenon lamp, emits white light. The spectral distribution of the white light is generally uniform, and spreads over the range of visible light. The white light radiated from the lamp 32 enters an incident surface 14*a* of a light-guide 14 via a collecting lens 34. The light-guide 14 of a fiber-optic bundle, which is provided in the video-scope 10, directs light to the tip portion of the video-scope 10. The light exiting from the light-guide 14 is emitted from the tip portion of the video-scope 10 via a diffusion lens 16; thus, the observed portion is illuminated. Light reflected off the observed portion enters into a dichroic prism 20 disposed at the tip portion of the video-scope 10 via an objective lens 18.

The dichroic prism 20 divides the reflected light into light having wavelengths more than 500 nm, corresponding to blue color; and light having wavelengths equal to or less than 500 nm, corresponding to green and red colors. The light corresponding to blue color is directed to a first CCD 12A, whereas the light corresponding to green and red colors is directed to a second CCD 12B.

A first color filter 13A, which transmits light having the first wavelength range, is provided on the front of a photo-receiving area of the first CCD 12A, on the other hand, a second color filter 13B, which transmits light having the second wavelength range, is provided on the front of a photo-receiving area of the second CCD 12B. A CCD driver 17 outputs clock pulse signals having a given frequency to the first and second CCDs 12A and 12B, so that image-pixel signals are successively read from the first and second CCDs 12A and 12B, respectively. Image-pixel signals that are read from the CCD 12A are fed to a narrow-band signal processor 36 and to a normal-image signal processor 40. On the other hand, image-pixel signals that are read from the CCD 12B are fed to an auto-fluorescent signal processor 38 and to the normal-image signal processor 40. In the present embodiment, the on-chip color filter method is applied as the imaging process method.

In the normal-image signal processor 40, based on image-pixel signals fed from the first CCD 12A and image-pixel signals fed from the second CCD 12B, video signals depending upon a video standard (hereinafter, called "normal image video signals"), such as NTSC signals, are generated to display a normal full-color image. In the narrow-band signal processor 36, based on image-pixel signals read from the CCD 12A, video signals for displaying the narrow-band image (hereinafter, called "NBI video signals") are generated. Then, in the auto-fluorescent signal processor 38, based on image-pixel signals read from the CCD 12B, video signals for displaying the auto-fluorescent image (hereinafter, called "auto-fluorescent video signals") are generated. Note that, in the auto-fluorescent signal processor 38, an amplifying process is also performed, since the intensity of the auto-fluorescence is weak.

A blue color filter 48 is a plate-shaped filter that transmits only excitation-light. A motor 46 moves the blue color filter 48 such that the blue color filter 48 is selectively positioned at positions on the light-path and off the light-path. A mode button 19 is provided on the video-scope 10 to change the observation mode. Herein, a normal observation mode that displays the normal image, or a special observation mode that displays the auto-fluorescent image and the narrow-band image, is selectively set. When the mode button 19 is operated, a detecting signal is fed to the system control circuit 44.

A switch circuit 42 selectively outputs one of the normal image video signals generated in the normal image signal processor 40, and two video signals; namely, the NBI video signals generated in the narrow-band signal processor 36, and the auto-fluorescent video signals generated in the auto-fluorescent signal processor 38. The system control circuit 44 controls the video-processor 30, and outputs control signals to the CCD driver 17, the switch circuit 42, the lamp 32, and other system components. Data including scope information, which is stored in a ROM 15 of the video-scope 10, is fed to the system control circuit 44.

With reference to FIGS. 2 to 9, the characteristics of the first and second color filters 13A and 13B are explained.

Figure 2:
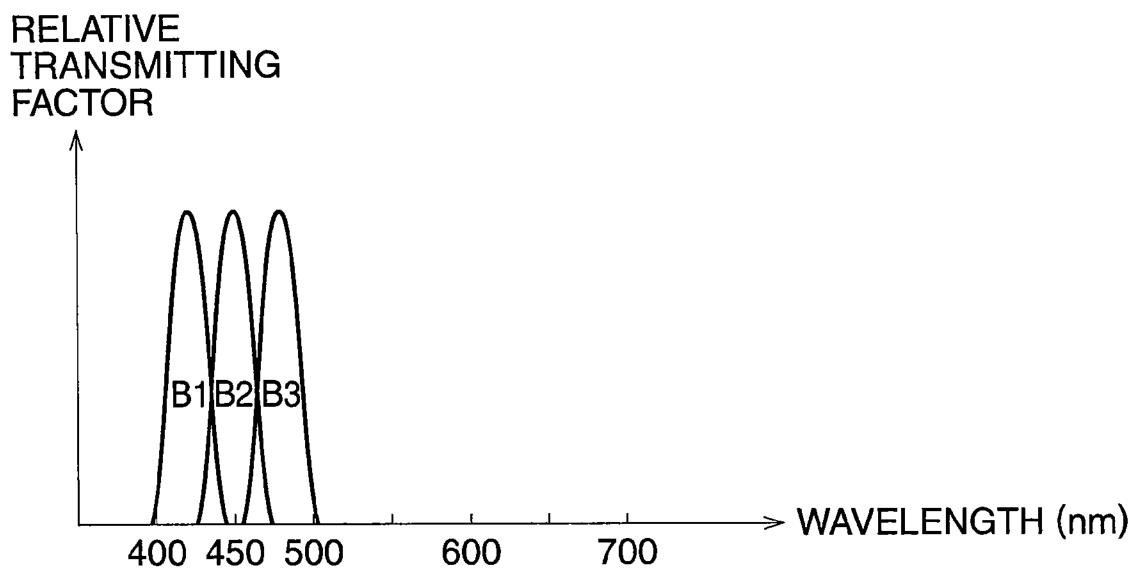
FIG. 2 is a view showing the spectral transmitting characteristics of a first color filter.
Figure 3:
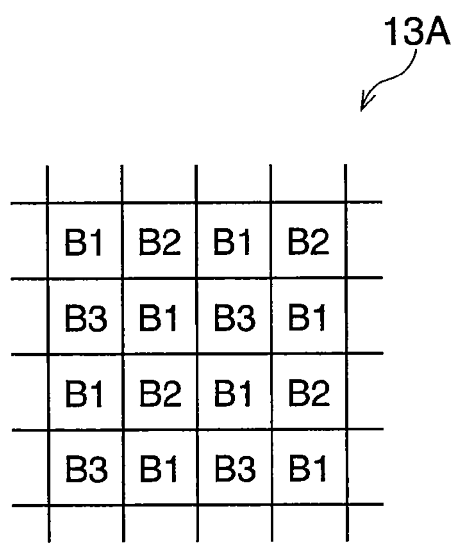
FIG. 3 is a view showing the color element array of the first color filter 13A.

FIG. 2 is a view showing the spectral transmitting characteristics of the first color filter 13A. FIG. 3 is a view showing the color element array of the first color filter 13A.

Three color elements B1, B2, and B3 are arrayed so as to be checkered, as shown in FIG. 3. In FIG. 2, distributed curved lines of the three color elements B1, B2, and B3, which have spectral peak levels 420 nm, 450 nm, and 480 nm and have given wavelength ranges, respectively, is shown. The wavelength ranges or bands of the color elements B1, B2, and B3 are set to the ranges of approximately 400 nm to 440 nm, approximately 430 nm to 470 nm, and approximately 460 nm to 450 nm, respectively. The adjacent distributed curved lines partially overlap one another.

Figure 4:
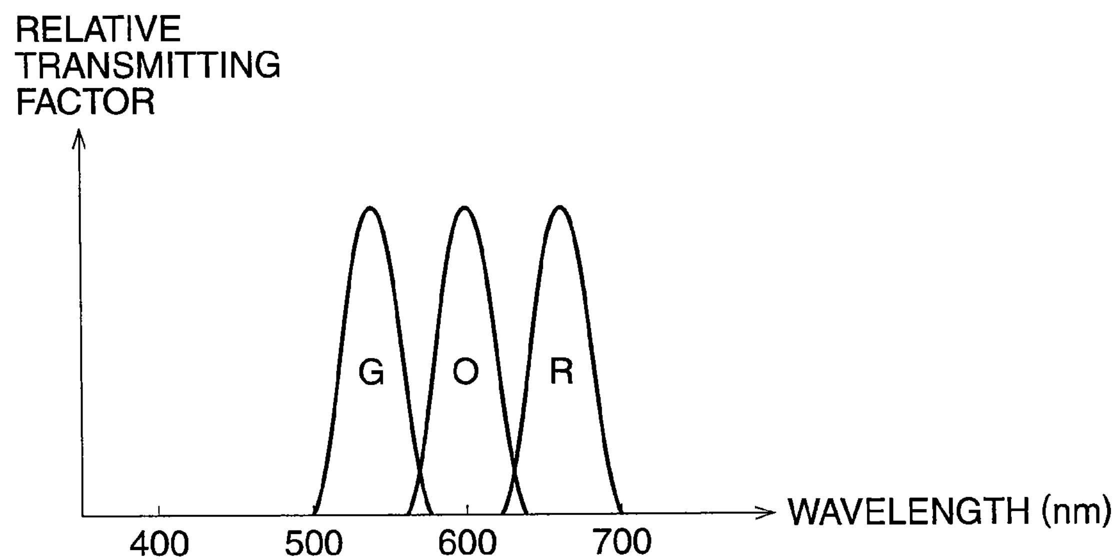
FIG. 4 is a view showing the spectral transmitting characteristics of a second color filter.
Figure 5:
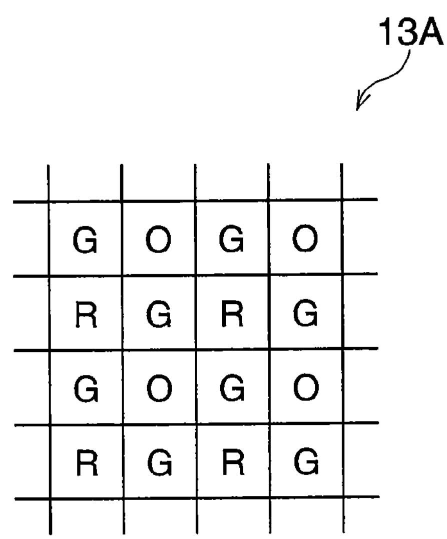
FIG. 5 is a view showing the color element array of the second color filter 13B.

FIG. 4 is a view showing the spectral transmitting characteristics of the second color filter 13B. FIG. 5 is a view showing the color element array of the second color filter 13B.

Three color elements G, O, and R are arrayed so as to be checkered, as shown in FIG. 5. In FIG. 4, distributed curved lines of the three color elements G, O, and R, which have spectral peak levels 540 nm, 600 nm, and 660 nm and have the given wavelength ranges, respectively, is shown. The wavelength ranges or bands of the color elements G, O, and R are set to the ranges of approximately 500 nm to 580 nm, approximately 560 nm to 640 nm, and approximately 620 nm to 700 nm, respectively. The adjacent distributed curved lines partially overlap one another.

In the case of the normal observation mode, the blue filter 48 is moved off the light-path. Consequently, white light emitted from the lamp 32 directly enters into the light-guide 14, and the reflected light entered into the dichroic prism 20 is divided into light having wavelengths longer than 500 nm and light having wavelengths equal to or shorter than 500 nm. Since the first color filter 13A transmits the light having wavelengths longer than 500 nm and the second color filter 13B transmits the light having wavelengths equal to or shorter than 500 nm (see FIGS. 2 and 4), image-pixel signals corresponding to the blue color are generated in the first CCD 12A by mixing a series of image-pixel signals corresponding to the color elements B1, B2, and B3, whereas image-pixel signals corresponding to the green and red colors are generated in the second CCD 12B.

Then, in the normal image signal processor 40, based on the image-pixel signals read from the first CCD 12A and the image-pixel signals read from the second CCD 12B, the normal image video signals are generated. The video signal circuit 42 outputs the normal image video signals to the monitor 70. Thus, the normal observation image is displayed on the monitor 70.

Figure 6:
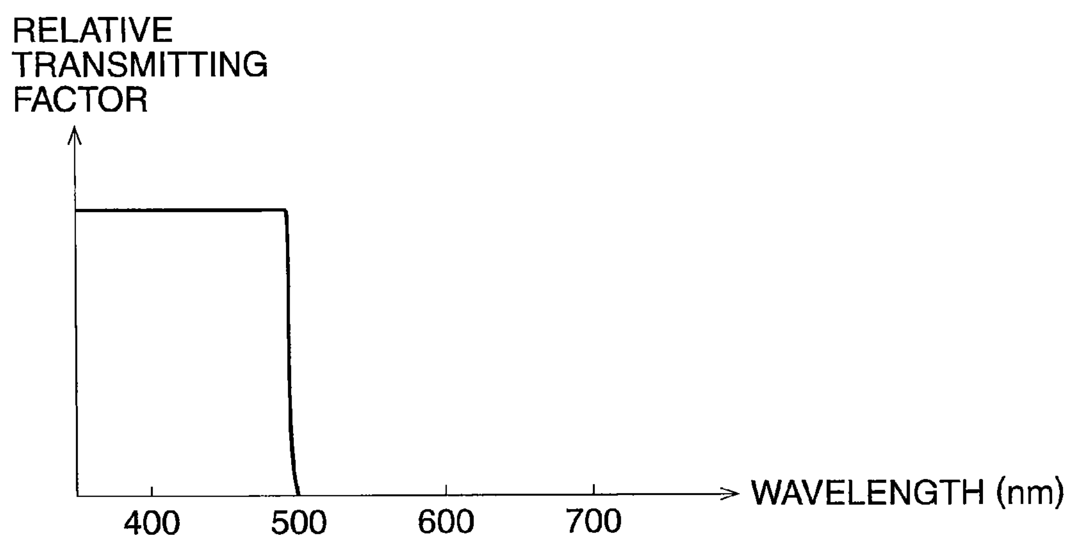
FIG. 6 is a view showing the spectral transmitting characteristics of a blue color filter.
Figure 7:
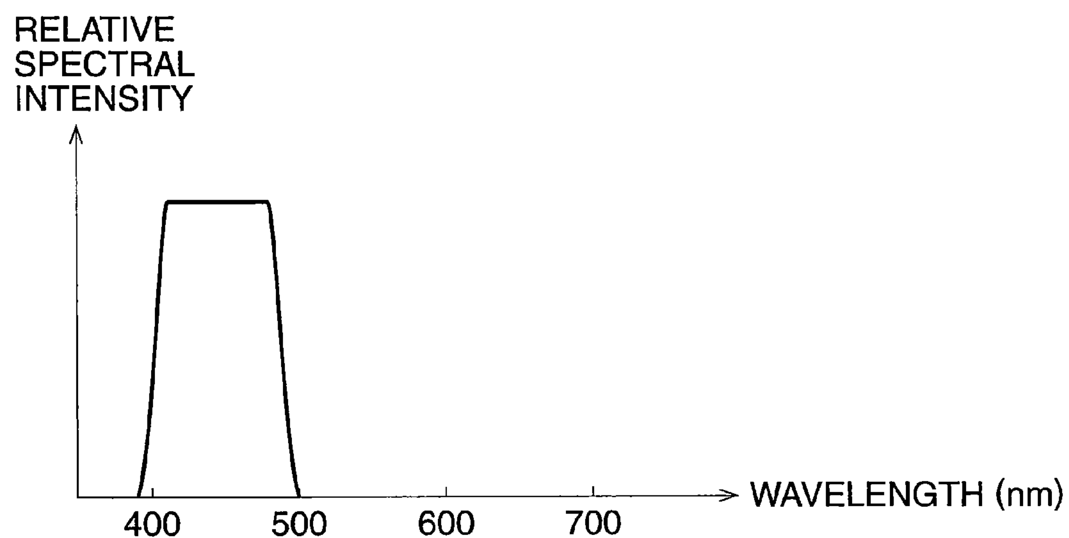
FIG. 7 is a view showing the spectral distribution characteristics of light passing through the blue color filter.
Figure 8:
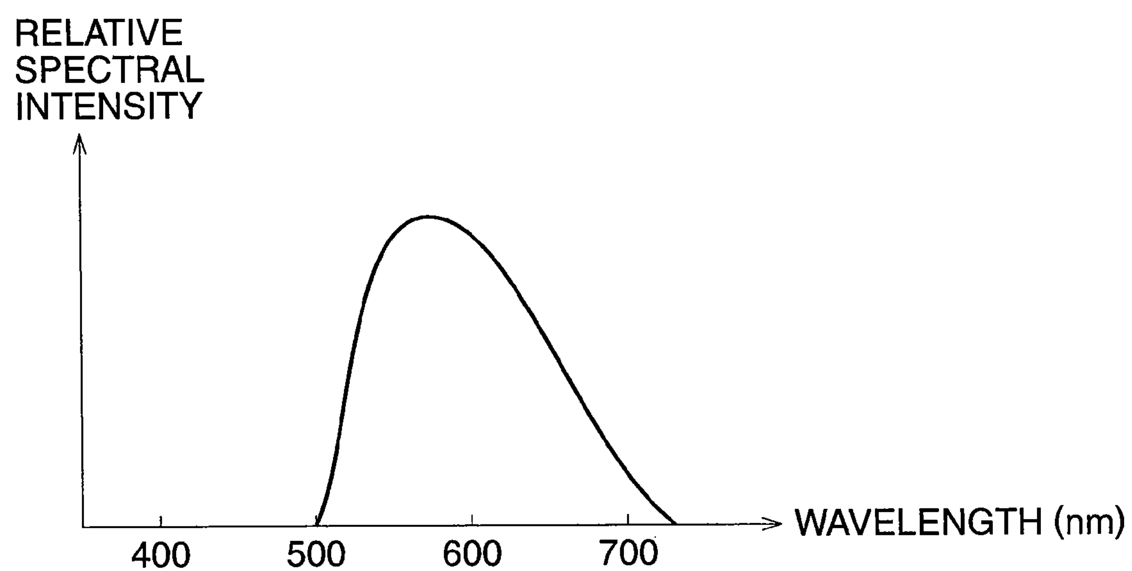
FIG. 8 is a view showing the spectral distribution characteristics of auto-fluorescent light.

FIG. 6 is a view showing the spectral transmitting characteristics of the blue color filter 48. FIG. 7 is a view showing the spectral distribution characteristics of light passing through the blue color filter 48; namely, excitation-light. FIG. 8 is a view showing the spectral distribution characteristics of auto-fluorescent light.

In the case of the special observation mode, the blue color filter 48 having the spectral transmitting characteristics shown in FIG. 6 is positioned on the light-path. Consequently, light having the spectral distribution characteristics shown in FIG. 7 (namely, light having the range of wavelengths of 400 nm to 500 nm) is irradiated on the observed portion as "excitation-light", and the auto-fluorescent light having the spectral distribution characteristics shown in FIG. 8 is irradiated from the observed portion.

As shown in FIG. 1, the reflected light of the excitation-light is directed to the first CCD 12A by the dichroic prism 20, and passes through the first color filter 13A. The first color filter 13A has the spectral transmitting characteristics shown in FIG. 2. On the other hand, the auto-fluorescent light having the wavelength range of approximately 500 nm to 700 nm (see FIG. 8) is directed to the second CCD 12A by the dichroic prism 20, and passes through the second color filter 13B (see FIG. 4). Consequently, image-pixel signals corresponding to the narrow-band image are generated in the first CCD 12A, and image-pixel signals corresponding to the auto-fluorescent image are generated in the second CCD 12B.

In the narrow-band signal processor 36, the NBI video signals are generated on the basis of the image-pixel signals read from the first CCD 12A; on the other hand, in the auto-fluorescent signal processor 38, the auto-fluorescent video signals are generated on the basis of the image-pixel signals read from the second CCD 12B. In the video signal circuit 42, an image process is performed on the NBI video signals and the auto-fluorescent video signals to display the narrow-band image and the auto-fluorescent image simultaneously and separately. The processed video signals are output to the monitor 70.

Figure 9A:
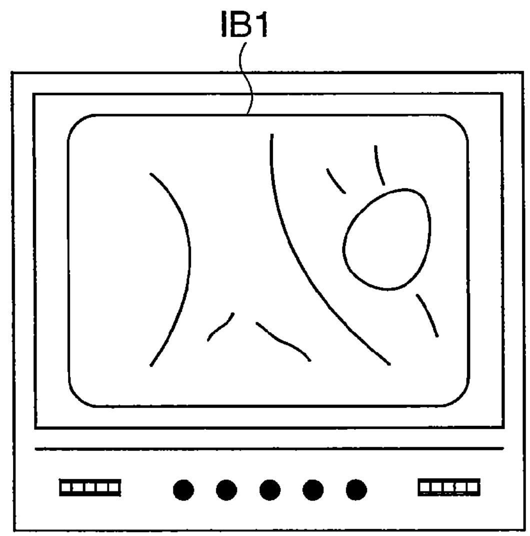
FIGS. 9A and 9B are views showing a screen of the monitor 70.
Figure 9B:
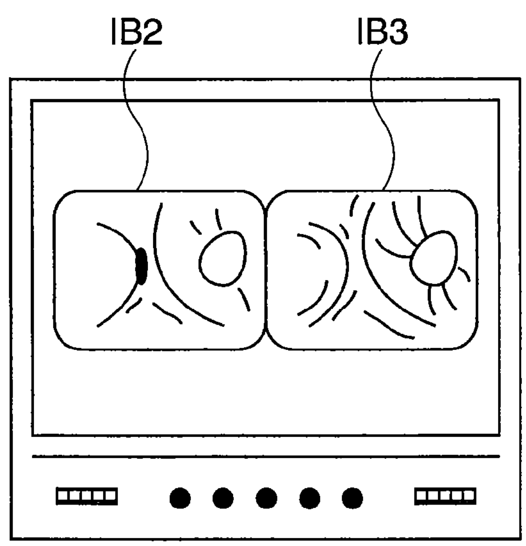

FIGS. 9A and 9B are views showing a screen of the monitor 70. In FIG. 9A, a screen in which the normal observation image is displayed is shown. In FIG. 9B, a screen in which the narrow-band image and the auto-fluorescent image are displayed is shown.

Figure 10:
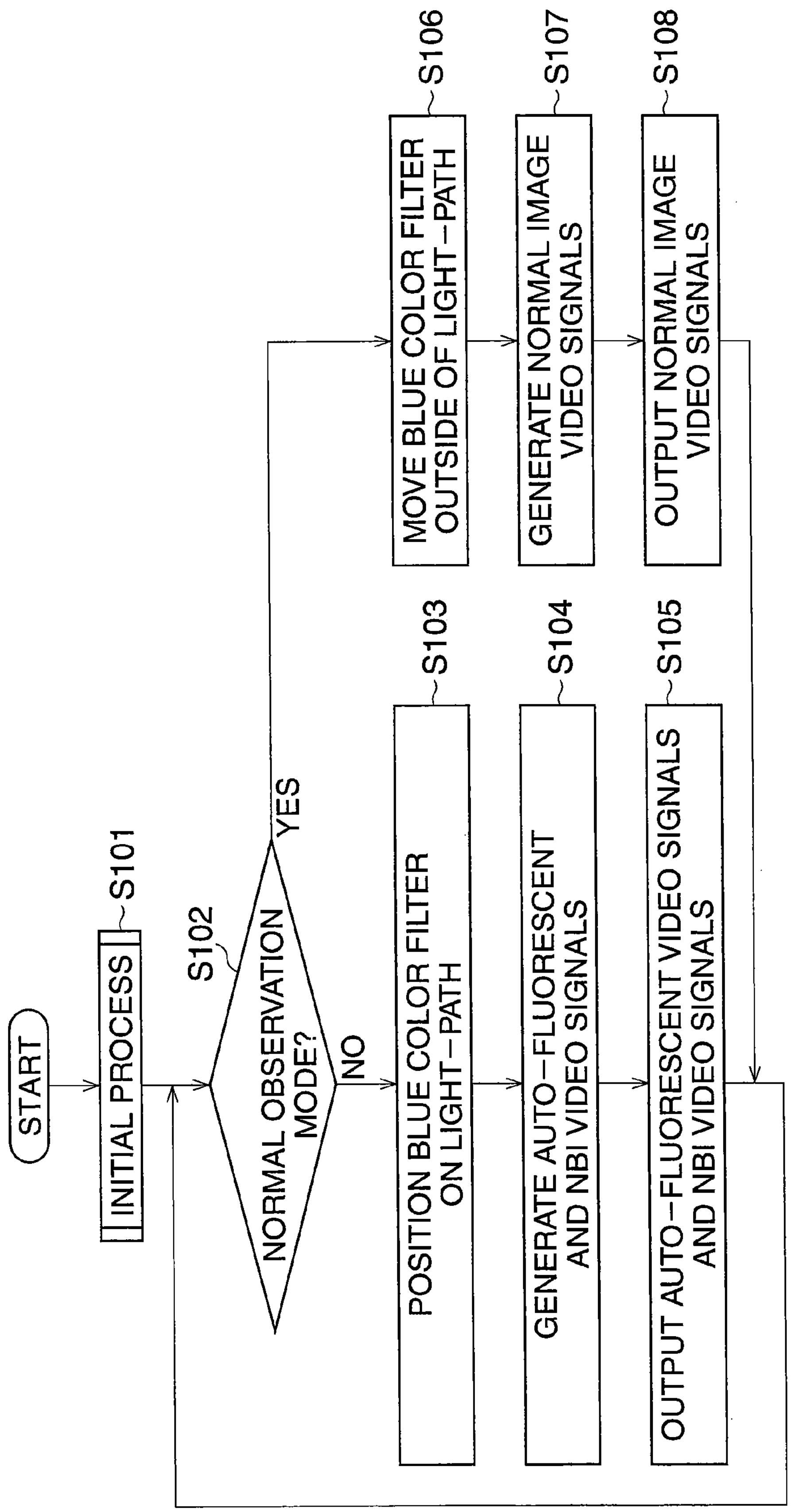
FIG. 10 is a flowchart of a main process performed by a video-processor.
Figure 11:
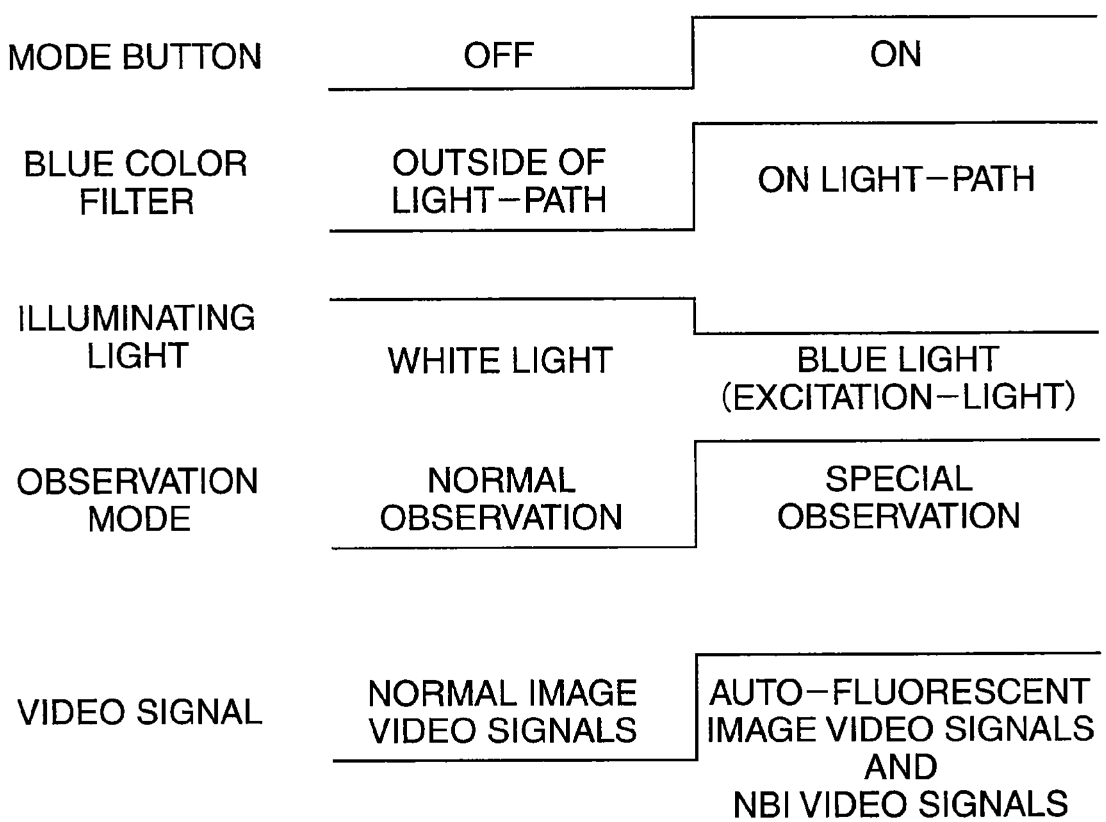
FIG. 11 is a timing chart of the main process.

FIG. 10 is a flowchart of the main process performed in the video-processor 30. FIG. 11 is a timing chart of the main process.

In Step S101, an initial process is performed on each circuit by turning the electric power ON. In Step S102, it is determined whether the normal observation mode is selected by operating the mode button 19.

When it is determined that the normal observation mode is selected, in Step S102, the process goes to Step S106, in which the blue color filter 48 is moved off the light-path. Then, in Step S107, the normal image video signals are generated in the normal image signal processor 40. In Step S108, the video signal circuit 42 is switched such that the normal image video signals are output to the monitor 70.

On the other hand, when it is determined that the special observation mode is selected in Step S102, the process goes to Step S103, in which the motor 46 drives the blue color filter 48 so that the blue color filter 48 is moved to a position on the light-path. In Step S104, the NBI video signals and the auto-fluorescent video signals are generated in the narrow-band signal processor 36 and the auto-fluorescent signal processor 38, respectively. In Step S105, the video signal circuit 42 is switched such that the NBI video signals and the auto-fluorescent video signals are output to the monitor 70.

In this manner, in the first embodiment, the dichroic prism 20, the first CCD 12A with the first color filter 13A, and the second CCD 12B with the second color filter 13B are provided at the tip portion 10A of the video-scope 10. The first color filter 13A transmits only light having wavelengths equal to or shorter than 500 nm; therefore, the blue color signal components in the normal image video signals are obtained, and the narrow-band video signals are also obtained. The second color filter 13B transmits only light having wavelengths longer than 500 nm; thus, the blue color components and the red color components in the normal image video signals are obtained, and the auto-fluorescent video signals are also obtained. Since the on-chip color filter method (not the color sequential method such as R, G, and B sequential method) is applied, an observed image can be clearly displayed by a simple construction, and a blur does not occur in the obtained image. Further, the narrow-band image and the auto-fluorescent image are separately displayed.

In the first color filter 13A, as shown in FIG. 2, the three spectral peak levels of the three color elements B1, B2, and B3 are distributed at even intervals. Thus, a fine change of colors can be clearly represented in the narrow-band image so that colors in the observed portion can be faithfully reproduced. Similarly, in the second color filter 13B, as shown in FIG. 4, the three spectral peak levels of the three color elements G, O, and R are distributed at even intervals. Thus, a fine change of colors can be represented in the auto-fluorescent image.

With reference to FIGS. 12 to 15, a second embodiment is explained. The second embodiment is different from the first embodiment in that a laser is used, and a color filter composed of two color elements is used.

Figure 12:
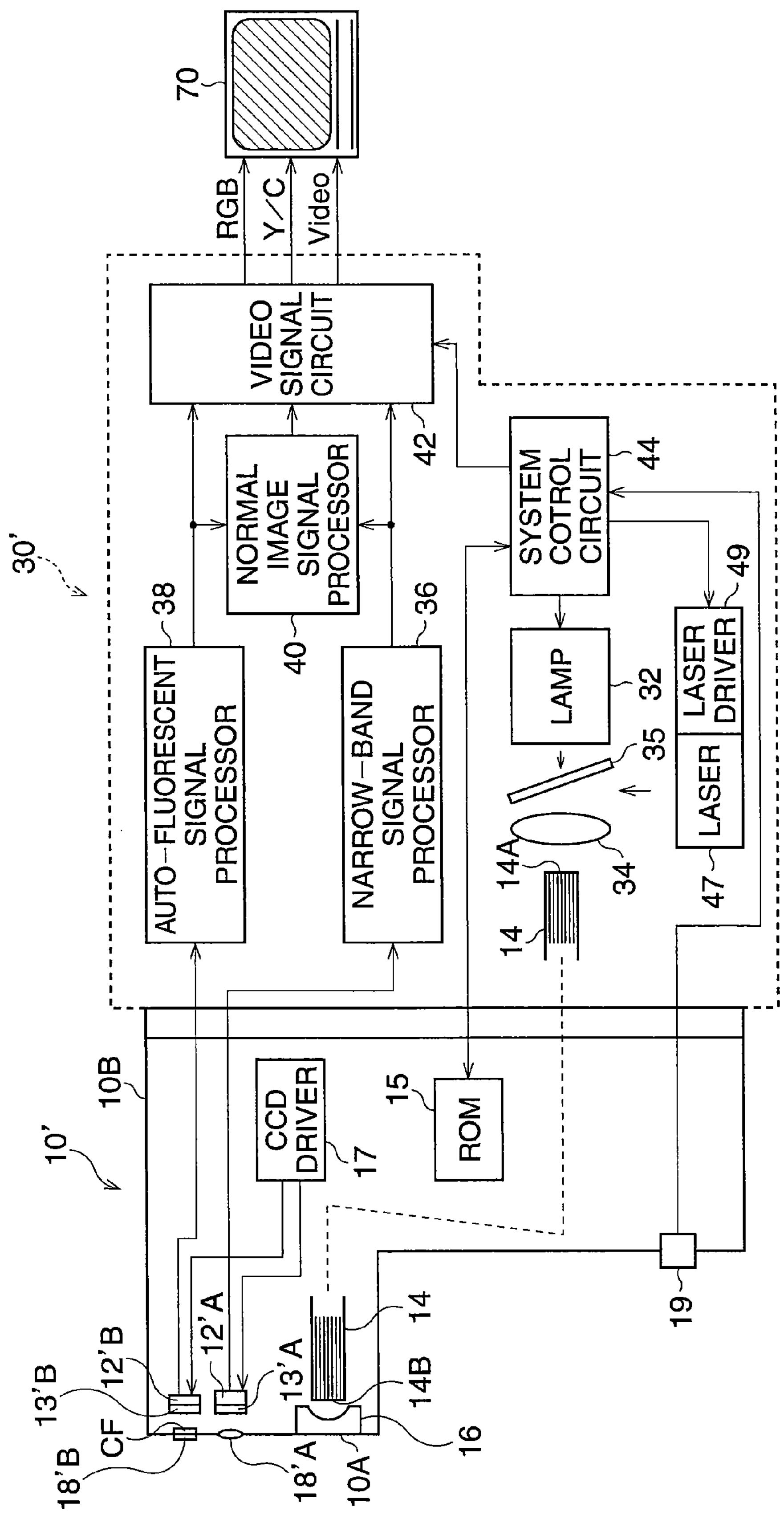
FIG. 12 is a block diagram of an electronic endoscope according to a second embodiment.

FIG. 12 is a block diagram of an electronic endoscope according to the second embodiment. A video-scope 10' has a first CCD 12'A and a second CCD 12'B, which are disposed in parallel so as to face the observed portion, and, further, has a first objective lens 18'A and a second objective lens 18'B, which are opposite the first CCD 13'A and the second CCD 13'B, respectively. The objective lens 18'B is covered with a cut-off filter CF, which blocks the excitation-light. In a processor 30', a half mirror 35, a laser 47, and a laser driver 49 are provided.

Figure 13:
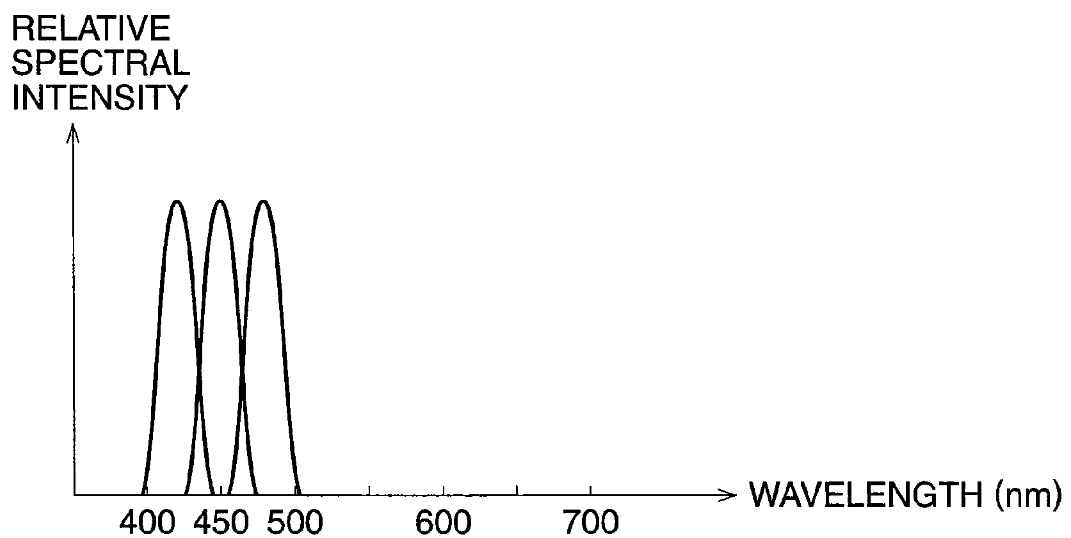
FIG. 13 is a view showing the spectral distribution characteristics of a laser.

FIG. 13 is a view showing the spectral distribution characteristics of the laser 47. The laser 47 emits light composed of three light components having peak levels of 408 nm, 445 nm, and 488 nm, respectively, as shown in FIG. 13. These spectral distribution characteristics correspond to the spectral transmitting characteristics of a color filter 13'A, which are the same as those of the color filter 13A shown in the first embodiment (see FIG. 2). The half mirror 35, which is disposed between the lamp 32 and the collective lens 34, transmits the white light from the lamp 32 to the incidence surface 14A of the light guide 14, and reflects the light or laser beam emitted from the laser 47, and directs the light to the incidence surface 14A of the light guide 14.

Figure 14:
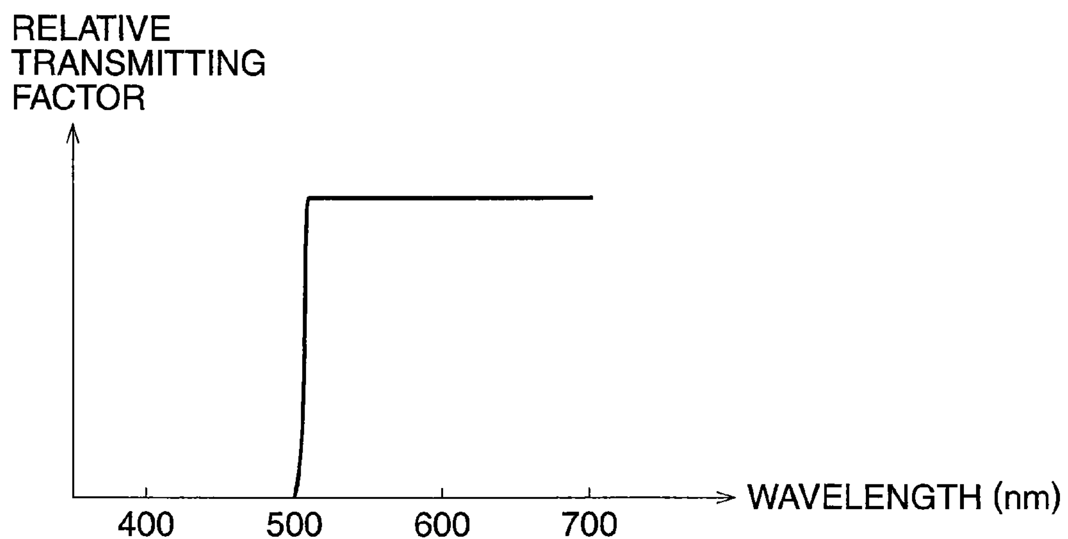
FIG. 14 is a view showing the spectral transmitting characteristics of a cut-off filter.

FIG. 14 is a view the showing spectral transmitting characteristics of the cut-off filter CF. As shown in FIG. 14, the cut-off filter CF transmits only light having wavelengths longer than 500 nm. Thus, the reflected light of the excitation-light is blocked by the cut-off filter CF.

Figures 15, 16:
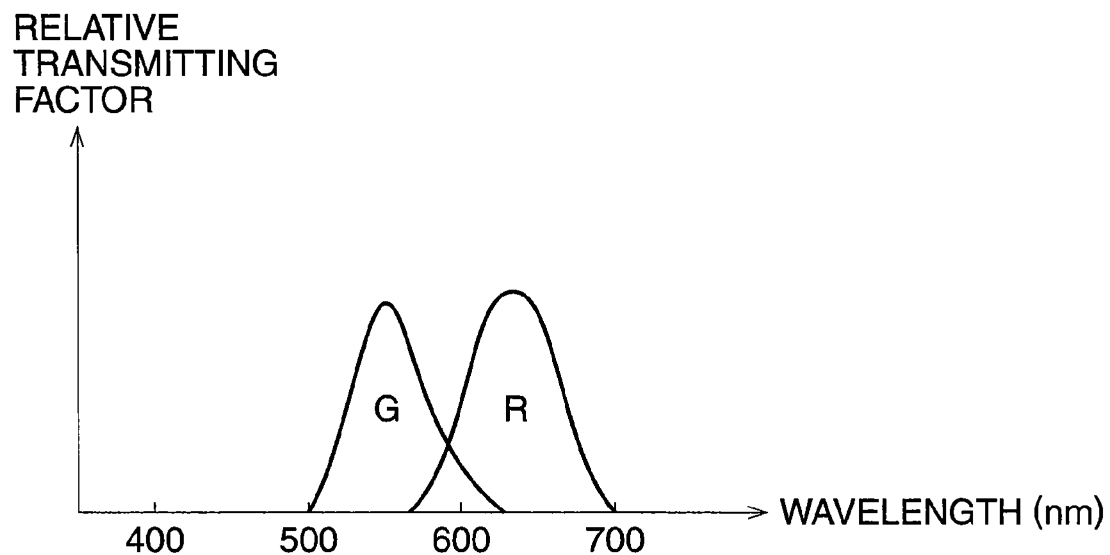
FIG. 15 is a view showing the spectral transmitting characteristics of a second color filter according to the second embodiment.
FIG. 16 is a view showing the color element array of the second color filter.

FIG. 15 is a view showing the spectral transmitting characteristics of the second color filter 13'B. FIG. 16 is a view showing the color element array of the second color filter 13'B.

As shown in FIG. 16, the color filter 13'B is composed of checkered color elements "G" and "R". The spectral transmitting characteristics are represented by a distributed curved line having a spectral peak level at wavelength of 550 nm, and a distributed curved line having spectral a peak level at wavelength of 650 nm (see FIG. 15).

When the normal observation mode is selected, the laser 47 is controlled so as not to emit the laser beam. The observed portion is illuminated by the light emitted from the lamp 32. In the CCD 12'A, light of short-wavelengths (namely, light corresponding to the blue color (B)) reaches the photo-receiving area by the color filter 13'A that is the same as the first color filter 13A shown in the first embodiment (see FIG. 2). On the other hand, in the CCD 12'B, light of long-wavelengths (namely, light corresponding to green color (G) and red color (R)) reaches the photo-receiving area by the cut-off filter CF and the second color filter 13'B (see FIGS. 14 and 15). Consequently, similarly to in the first embodiment, the normal image video signals are generated in the normal image signal processor 40, and the normal observation image is displayed on the monitor 70.

When the special observation mode is selected, the laser 47 is enabled and the lamp 32 is turned OFF, so that the laser beam is irradiated on the observed portion. The reflected light is cut off by the cut-off filter CF, and the second color filter 13'B transmits only light having a wavelength longer than 500 nm (see FIG. 15). On the other hand, the color filter 13'A transmits light having a wavelength shorter than 500 nm; namely, the reflected light of the excitation-light (see FIG. 2). Therefore, the reflected light of the excitation-light reaches the photo-receiving area of the first CCD 12'A, and the auto-fluorescent light reaches the photo-receiving area of the second CCD 12'B.

In the narrow-band signal processor 36 and the auto-fluorescent signal processor 38, similarly to in the first embodiment, the NBI video signals and the auto-fluorescent video signals are generated, so that the narrow-band image and the auto-fluorescent image are both displayed on the monitor 70.

Optionally, the first color filter may transmit light having short wavelength corresponding to blue color. The second color filter may transmit light having middle and long wavelength corresponding to green and red colors. The number of color elements may be optionally set.

Finally, it will be understood by those skilled in the arts that the foregoing description is of preferred embodiments of the device, and that various changes and modifications may be made to the present invention without departing from the spirit and scope thereof.

The present disclosure relates to subject matter contained in Japanese Patent Application No. 2005-237392 (filed on Aug. 18, 2005), which is expressly incorporated herein, by reference, in its entirety.

The invention claimed is:

1. An electronic endoscope comprising:

a video-scope that has a first image sensor and a second image sensor;

a light supplier that selectively irradiates white light and excitation-light on an observed portion;

a first color filter that is positioned on said first image sensor, is disposed along a light-path oriented toward said first image sensor, and has spectral transmitting characteristics that transmit light having a first wavelength range corresponding to blue color;

a second color filter that is positioned on said second image sensor, is disposed along a light-path oriented toward said second image sensor, and has spectral transmitting characteristics that transmit light having a second wavelength range corresponding to green and red colors;

a first signal processor that generates normal image video signals corresponding to a normal observation image on the basis of image-pixel signals that are read from said first and second image sensors by the white light;

a second signal processor that generates narrow-band video signals corresponding to a narrow-band image on the basis of image-pixel signals that are read from said first image sensor by reflected light of the excitation-light; and a third signal processor that generates auto-fluorescent video signals corresponding to an auto-fluorescent image on the basis of image-pixel signals that are read from said second image sensor by auto-fluorescent light emitted from the observed portion.

2. The electronic endoscope of claim 1, wherein the first wavelength range is set to a range that does not exceed a boundary wavelength in a range between 450 nm and 550 nm, said second wavelength range being set to a range that exceeds the boundary wavelength.

3. The electronic endoscope of claim 1, wherein said first color filter comprises a first plurality of color elements that have different spectral peak levels in a plurality of distributed curved lines defined by said plurality of color elements.

4. The electronic endoscope of claim 3, wherein said first color filter comprises three color elements that have spectral peak levels distributed at even intervals.

5. The electronic endoscope of claim 1, wherein said second color filter comprises a second plurality of color elements that have different spectral peak levels in a plurality of distributed curved lines defined by said plurality of color elements.

6. The electronic endoscope of claim 5, wherein said second color filter comprises two or three color elements that have spectral peak levels distributed at even intervals.

7. The electronic endoscope of claim 1, further comprising:

one objective optical system that forms an object image; and a beam splitter that divides light passing through said objective optical system into light having the first wavelength range and light having the second wavelength range, an object image being formed on said first image sensor by the light having the first wavelength range, an object image being formed on said second image sensor by the light having the second wavelength range.

8. The electronic endoscope of claim 1, further comprising:

a first objective optical system that faults an object image on said first image sensor; and a second objective optical system that forms an object image on said second image sensor.

9. The electronic endoscope of claim 8, further comprising a cut-off filter that is disposed at the front of said second objective optical system, and that blocks the light having the first wavelength range.

10. The electronic endoscope of claim 1, wherein said light supplier comprises:

a light source that emits white light having spectral transmitting characteristics in which spectrum is distributed over wavelengths of visible light;

an excitation-light color filter that transmits light having a wavelength range corresponding to the excitation-light; and a color filter driver that selectively positions said excitation-light color filter on a light-path and off the light-path.

11. The electronic endoscope of claim 10, wherein said color filter driver positions said excitation-light color filter off a light-path when a normal observation mode for displaying the normal observation image is set, and positions said excitation-light color filter on the light-path when a special observation mode for displaying the auto-fluorescent image and the narrow-band image is set.

12. The electronic endoscope of claim 1, wherein said light source comprises:

a white light source that emits white light having spectral transmitting characteristics in which spectrum is distributed over wavelengths of visible light;

a laser that emits the excitation-light;

an optical system that directs the excitation-light to a light-path of the white light; and a laser driver that turns said laser ON/OFF.

13. The electronic endoscope of claim 12, wherein said laser driver turns said laser OFF when a normal observation mode for displaying the normal observation image is set, and turns said laser ON when a special observation mode for displaying the auto-fluorescent image and the narrow-band image is set.

14. The electronic endoscope of claim 1, further comprising a fourth signal processor that processes the auto-fluorescent video signals and the NBI video signals so as to display the auto-fluorescent image and the narrow-band image on a monitor simultaneously and separately.

15. The electronic endoscope of claim 1, further comprising a fifth signal processor that selectively outputs one of the normal image video signals and a set of the NBI video signals and auto-fluorescent video signals.

16. The electronic endoscope of claim 1, further comprising a change member that is operated to set a normal observation mode for displaying the normal observation image or the set a special observation mode for displaying the auto-fluorescent image and the narrow-band image.

17. The electronic endoscope according to claim 1, said first signal processor, said second signal processor and said third signal processor being configured to process the image pixel signals by an on-chip color filter method.

* * * * *